US009611226B2

(12) United States Patent
Wang et al.

(10) Patent No.: US 9,611,226 B2
(45) Date of Patent: Apr. 4, 2017

(54) PREPARATION METHOD FOR AZOXYSTROBIN

(71) Applicants: NUTRICHEM COMPANY LIMITED, Beijing (CN); SHANGYU NUTRICHEM CO., LTD., Zhejiang (CN)

(72) Inventors: Wenjun Wang, Beijing (CN); Jianwei Chen, Beijing (CN); Jianhong Chi, Beijing (CN); Yongchang Zhao, Beijing (CN); Xufang Deng, Beijing (CN); Long Wang, Beijing (CN); Hua'nan You, Beijing (CN)

(73) Assignees: Nutrichem Company Limited, Beijing (CN); Shanqyu Nutrichem Co., Ltd., Shangyu (CN)

( * ) Notice: Subject to any disclaimer, the term of this patent is extended or adjusted under 35 U.S.C. 154(b) by 0 days.

(21) Appl. No.: 14/889,299

(22) PCT Filed: Mar. 20, 2014

(86) PCT No.: PCT/CN2014/073733
§ 371 (c)(1),
(2) Date: Nov. 5, 2015

(87) PCT Pub. No.: WO2014/183502
PCT Pub. Date: Nov. 20, 2014

(65) Prior Publication Data

US 2016/0090365 A1 Mar. 31, 2016

(30) Foreign Application Priority Data

May 16, 2013 (CN) .......................... 2013 1 0182260

(51) Int. Cl.
*C07D 239/52* (2006.01)

(52) U.S. Cl.
CPC ................................ *C07D 239/52* (2013.01)

(58) Field of Classification Search
CPC .................................................. C07D 239/52
See application file for complete search history.

(56) References Cited

U.S. PATENT DOCUMENTS

| | | | |
|---|---|---|---|
| 8,124,761 B2 | 2/2012 | Whitton et al. | |
| 8,552,185 B2 | 10/2013 | Beveridge et al. | |
| 2008/0214587 A1 | 9/2008 | Whitton et al. | |
| 2010/0036124 A1 | 2/2010 | Beveridge et al. | |
| 2010/0063275 A1* | 3/2010 | Beveridge ............ | C07D 239/52 544/2 |
| 2016/0090365 A1 | 3/2016 | Wang et al. | |

FOREIGN PATENT DOCUMENTS

| | | | |
|---|---|---|---|
| CN | 1047286 | A | 11/1990 |
| CN | 102311392 | A | 1/2012 |
| CN | 102070538 | B | 5/2012 |
| CN | 102690237 | A | 9/2012 |
| EP | 3042896 | A1 | 7/2016 |
| WO | 2008/043977 | A1 | 4/2008 |
| WO | 2008/075341 | A1 | 6/2008 |

OTHER PUBLICATIONS

International Search Report for International Application No. PCT/CN2014/073733, mailed Jul. 1, 2014, 4 pages.
Written Opinion for International Application No. PCT/CN2014/073733, mailed Jul. 1, 2014, 5 pages.

* cited by examiner

*Primary Examiner* — Valerie Rodriguez-Garcia
(74) *Attorney, Agent, or Firm* — Husch Blackwell LLP

(57) ABSTRACT

Disclosed in the present invention is a preparation method of azoxystrobin having a structure as shown by formula (1), the method comprising: a) performing an etherification reaction by reacting the compound having a structure shown by formula (2) with 2-cyanophenol and/or a salt thereof under the catalysis of an azabicyclo tertiary amine compound and/or a salt thereof as the catalyst in a butyl acetate medium to obtain a butyl acetate solution containing azoxystrobin; and b) cooling the butyl acetate solution containing azoxystrobin to precipitate Azoxystrobin having a structure as shown by formula (1) from the butyl acetate solution. Using the method provided by the present invention to prepare azoxystrobin can significantly improve the yield of azoxystrobin, and can obtain azoxystrobin products having high purity.

(1)

(2)

6 Claims, No Drawings

PREPARATION METHOD FOR AZOXYSTROBIN

FIELD OF THE INVENTION

The present invention relates to a preparation method for azoxystrobin.

BACKGROUND OF THE INVENTION

As a high efficient and broad spectrum bactericide, azoxystrobin is widely used for preventing and treating a variety of plant diseases.

WO92/08703 disclosed an azoxystrobin synthesis method. In that method, a chemical compound with a structure represented by formula (2) has an etherification reaction with 2-hydroxyphenol and potassium carbonate in a polar solvent (in particular N,N-dimethyl formamide), with a copper halide as the catalyst; after the reaction, the reaction mixture is filtered and washed with N,N-dimethyl formamide, and is treated by reduced pressure distillation under 70° C. water bath condition to obtain a crude product; then, the crude product is dissolved in methanol by refluxing, and is cooled to 0-5° C. for crystallization; finally, the crystallized product is washed with petroleum ether and vacuum-dried at 50° C. to obtain a final product.

In the method disclosed in patent document WO2006/114572, allow a chemical compound with a structure represented by formula (2) to react with 2-cyanophenol and an acid acceptor in an inert solvent or diluent, with 1,4-diazabicyclo[2.2.2]-octane as the catalyst; after the reaction, the reaction mixture is cooled to 70-75° C. and keep the temperature by adding water slowly into the reaction mixture, and stir the reaction mixture at 75° C., kept standing, and then remove the aqueous phase; next, water is added into the reaction mixture again and then remove the aqueous phase, to obtain an organic phase that contains the product.

In the method disclosed in patent document WO2008/075341, allow a chemical compound with a structure represented by formula (2) to react with 2-cyanophenol and a hydroxide or carbonate of an alkali metal in a solvent (preferably DMF, DMAA, or DMSO), with a copper chloride as the catalyst; after the reaction, the solvent is removed by evaporation, and then butyl acetate and water are added into the reaction mixture to obtain an organic phase and an aqueous phase; next, the aqueous phase is removed, and crystallize azoxystrobin from the organic phase by cooling; then, the solid azoxystrobin is obtained by filtering and is washed with methanol, to obtain an azoxystrobin product at 98-99% purity.

The above-mentioned etherification reaction processes in the prior art usually happen in an aprotic polar solvent, the solvent is removed after the reaction, and then an organic solvent is utilized to crystallize the product from the organic solvent. A drawback of those processes is: the high water-solubility of the aprotic polar solvent brings difficulties in the follow-up product separation and recovery procedure; especially, in a case that the solvent of etherification reaction is removed by distillation, the product precipitates heavily after a great part of solvent is removed by distillation; consequently, the stirring in the distillation process is hindered, and the heat transfer in the reaction system is poor; hence, a considerable part of solvent can't be recovered and finally enters into the environment, resulting in increased production cost and environmental pollution. In addition, since the reactant 2-cyanophenol and/or its salt in the above-mentioned etherification reaction process can be oxidized easily and thereby produces tar, and the compound with a structure represented by formula (2) tends to aggregate and hydrolyze, resulting in very low content of azoxystrobin in the crude product obtained from the reaction, usually the product has to be treated with an appropriate solvent for recrystallization in order to obtain a product at higher purity; moreover, the purity of the obtained azoxystrobin product is low, usually lower than 98%. Owing to the fact that azoxystrobin products are heavily applied globally, a huge amount of impurities applied along with azoxystrobin enters into the environment, which brings a potential threat to environmental safety.

SUMMARY OF THE INVENTION

The object of the present invention is to provide an innovative preparation method for azoxystrobin, with which the yield ratio of azoxystrobin can be significantly improved, and an azoxystrobin product at high purity can be obtained.

The applicant of the present invention has found surprisingly in the research: butyl acetate solvent not only can bring a favorable recrystallization effect to the product but also can be used as a reacting solvent and the reaction effect is good. In that way, not only the industrial operation can be simplified, but also the production efficiency can be improved.

Based on the above-mentioned finding, to realize the object described above, the present invention provides a method for preparing azoxystrobin with a structure represented by formula (1), comprising: a) allowing a chemical compound with a structure represented by formula (2) to have an etherification reaction with 2-cyanophenol and/or its salt in a butyl acetate medium, under the catalysis of an azabicyclo-tertiary amine compound and/or its salt that serves as a catalyst, to obtain a butyl acetate solution that contains azoxystrobin; b) cooling down the butyl acetate solution that contains azoxystrobin to precipitate the azoxystrobin with a structure represented by formula (1) from butyl acetate.

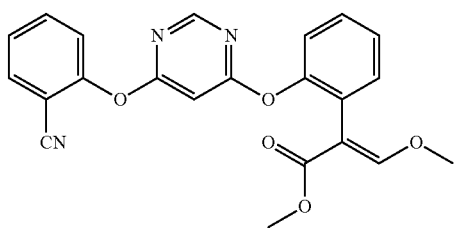

(1)

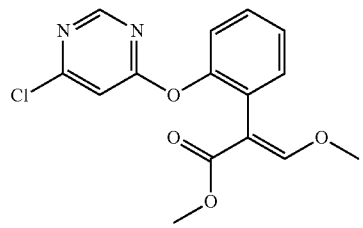

(2)

With the azoxystrobin preparation method provided in the present invention, the yield ratio of azoxystrobin can be increased significantly, and an azoxystrobin product at high purity can be obtained, this is mainly because: the method provided in the present invention utilizes butyl acetate as reaction solvent and recrystallization solvent; hence, the step of removing the etherification reaction solvent by evaporation is omitted, the crystallization process of the product is simplified, the impact of product precipitation in the evaporation process on stirring can be avoided, and environmental pollution incurred by incomplete removal of the solvent can be eliminated; moreover, with the method provided in the present invention, since azoxystrobin crystal with a structure represented by formula (1) can precipitate directly from butyl acetate, the operation of the method according to the present invention is more simple and convenient, and an azoxystrobin product at 99% or higher purity can be obtained.

DETAILED DESCRIPTION OF THE EMBODIMENTS

Hereunder the embodiments of the present invention will be detailed. It should be appreciated that the embodiments described here are only provided to describe and explain the present invention, but shall not be deemed as constituting any limitation to the present invention.

The present invention provides a method for preparing azoxystrobin with a structure represented by formula (1), comprising: a) allowing a chemical compound with a structure represented by formula (2) to have an etherification reaction with 2-cyanophenol and/or its salt in a butyl acetate medium, under the catalysis of an azabicyclo-tertiary amine compound and/or its salt that serves as a catalyst, to obtain a butyl acetate solution that contains azoxystrobin; b) cooling down the butyl acetate solution that contains azoxystrobin to precipitate the azoxystrobin with a structure represented by formula (1) from butyl acetate.

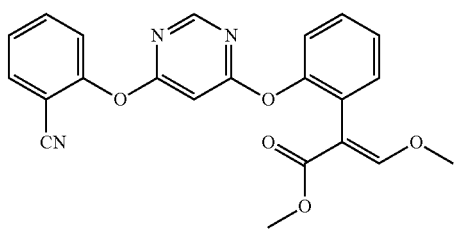

(1)

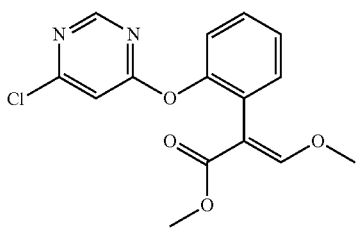

(2)

In the preparation method for azoxystrobin provided in the present invention, the azabicyclo-tertiary amine compound can be at least one of the compound represented by formula (3), the compound represented by formula (4), and the compound represented by formula (5);

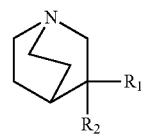

(3)

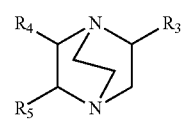

(4)

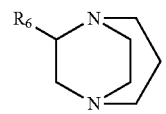

(5)

Wherein, in formula (3), preferably, $R_1$ and $R_2$ are hydrogen, hydroxyl, C1-C6 hydrocarbonyl, or C1-C6 oxyl independently of each other, or $R_1$ and $R_2$ are combined into a structure of carbonyl, thiocarbonyl, cycloalkyl thioether, cycloalkoxyl, or ketal; in the case that $R_1$ and $R_2$ are combined into one base group in formula (3), for example, when $R_1$ and $R_2$ are combined into carbonyl, the represented compound is the compound represented by formula (6); when $R_1$ and $R_2$ are combined into thiocarbonyl, the represented compound is the compound represented by formula (7); when $R_1$ and $R_2$ are combined into cycloalkoxyl, the represented compound is the compound with a structure represented by formula (8); when $R_1$ and $R_2$ are combined into cycloalkyl thioether, the represented compound is the compound with a structure represented by formula (9).

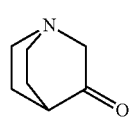

(6)

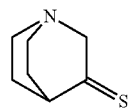

(7)

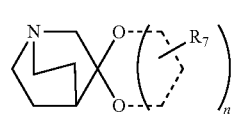

(8)

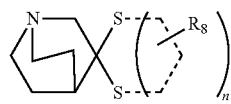

(9)

In formula (8), $R_7$ represents C1-C20 hydrocarbonyl, C3-C10 cycloalkyl, C1-C10 alkoxyl, or C3-C10 cycloalkoxyl, and n is an integer within 1-10 range.

In formula (9), $R_8$ represents C1-C20 hydrocarbonyl, C3-C10 cycloalkyl, C1-C10 alkoxyl, or C3-C10 cycloalkoxyl, and n is an integer within 1-10 range.

In formula (4), preferably, $R_3$, $R_4$, and $R_5$ are hydrogen, C1-C6 hydrocarbonyl, C1-C6 oxyl, dimethyl amino, diethyl amino, diisopropyl amino, cyano, fluorine, chlorine, or bromine independently of each other.

In formula (5), preferably, $R_6$ is hydrogen, C1-C6 hydrocarbonyl, C1-C6 oxyl, sulfhydryl, dimethyl amino, diethyl amino, diisopropyl amido, cyano, fluorine, chlorine, or bromine independently of each other.

Preferably, the azabicyclo-tertiary amine compound is at least one of 1-azabicyclo[2.2.2]octane, 1-azabicyclo[2.2.2] octane-8-ketone, 1'-azaspiro[1,3]dioxolane-2,3'-bicyclo [2.2.2]-octane, 1,4-diazabicyclo[2.2.2]octane, 2-methyl-1,4-diazabicyclo[2.2.2]octane, 2,6-dimethyl-1,4-diazabicyclo [2.2.2]octane, 2,5-dimethyl-1,4-diazabicyclo[2.2.2]octane, 1,5-diazabicyclo[3.2.2]nonane, and 6-methyl-1,5-diazabicyclo[3.2.2]nonane.

The salt of the azabicyclo-tertiary amine compound can be acid salt, preferably hydrochloride and/or sulfate.

In the process of reaction between the compound with a structure represented by formula (2) and 2-cyanophenol and/or a salt of 2-cyanophenol, corresponding to 1 mol compound with a structure represented by formula (2), the total usage amount of 2-cyanophenol and the salt of 2-cyanophenol can be 0.9-2 mol, preferably 1-1.8 mol. If 2-cyanophenol or a salt of 2-cyanophenol is used solely in the reaction process, the total usage amount of 2-cyanophenol and the salt of 2-cyanophenol refers to the usage amount of 2-cyanophenol or the usage amount of the salt of 2-cyanophenol; if both 2-cyanophenol and a salt of 2-cyanophenol are used in the reaction process, the total usage amount of 2-cyanophenol and the salt of 2-cyanophenol refers to the sum of the usage amount of 2-cyanophenol and the usage amount of the salt of 2-cyanophenol.

The salt of 2-cyanophenol is preferably an alkali salt of 2-cyanophenol. Optimally, the salt of 2-cyanophenol is sodium salt and/or potassium salt of 2-cyanophenol.

When 2-cyanophenol or a mixture of 2-cyanophenol and its salt is used as a raw material to have etherification reaction with the compound with a structure represented by formula (2), an alkali-metal hydroxide or alkali-metal carbonate can be added into the reaction system, or an alkali-metal hydroxide or alkali-metal carbonate can be used to have a contact reaction with 2-cyanophenol to produce a salt of 2-cyanophenol, and then add the produced salt of 2-cyanophenol into the reaction system. Corresponding to 1 mol 2-cyanophenol, the usage amount of the alkali-metal hydroxide can be 0.8-2 mol, and the usage amount of the alkali-metal carbonate can be 0.4-2 mol. The alkali metal is preferably sodium or potassium.

In the present invention, there is no particular restriction on the usage amount of the catalyst. Preferably, corresponding to 1 mol compound with a structure represented by formula (2), the total usage amount of azabicyclo-tertiary amine compound and its salt, which are used as the catalyst, is 0.0005-1 mol, preferably 0.02-0.05 mol. In the case that the usage amount of the catalyst is greater than or equal to 0.4 mol corresponding to 1 mol 2-cyanophenol, and an alkali-metal hydroxide or alkali-metal carbonate has to be added into the reaction system to allow 2-cyanophenol to convert to the salt of 2-cyanophenol, preferably the catalyst is added and mixed thoroughly to proceed etherification reaction after 2-cyanophenol reacts with an alkali-metal hydroxide or alkali-metal carbonate to fully produce the salt of 2-cyanophenol in the reaction system.

In the present invention, the usage amount of butyl acetate that is used as the solvent can be determined according to the usage amount of ordinary solvent. Preferably, in order to improve the mass transfer and heat transfer effect of the reaction, improve the yield ratio and purity of the reaction product, and simplify the follow-up operating procedure for azoxystrobin crystal with a structure represented by formula (1) obtained from the reaction, corresponding to 1 mol compound with a structure represented by formula (2), the usage amount of butyl acetate that is used as the reaction medium in the etherification reaction process is 100-5,000 ml, preferably 600-2,000 ml.

The preparation method provided in the present invention can be performed in any conventional reaction vessel and conventional conditions in the art for preparing azoxystrobin. Preferably, the reaction vessel is an glass line reactor kettle or stainless steel reactor kettle; the reaction conditions include: reaction temperature: 70-140° C., more preferably 80-120° C.; reaction pressure: atmospheric pressure. In addition, in order to improve the reaction rate and yield ratio, the reaction mixture can be stirred to improve the mass transfer and heat transfer effect in the reaction.

In the preparation method provided in the present invention, in order to enable the reaction to happen thoroughly, preferably all other components required for the etherification reaction, except the compound with a structure represented by formula (2) and the catalyst, are mixed thoroughly by stirring at 10-130° C. temperature to obtain a mixture that doesn't contain the compound with a structure represented by formula (2) and the catalyst, prior to the etherification reaction; then, the compound with a structure represented by formula (2) and the catalyst required for the reaction are added into the mixture at the temperature required for the etherification reaction, and the resulting mixture is mixed thoroughly for etherification reaction.

In the present invention, the purity of the compound with a structure represented by formula (2) for the etherification reaction is preferably not lower than 60 wt. %, more preferably not lower than 70 wt. %, even more preferably not lower than 80 wt. %.

The contact process described in the present invention is preferably maintained for a specific contact time within a specific temperature range, to enable the reaction to happen thoroughly. The contact time can be 2-8 h, preferably 3-5 h.

In the process of etherification reaction described in the present invention, the reaction situation can be monitored with a gas chromatograph. The reaction can be terminated when the gas chromatograph indicates that the normalized area of the compound with a structure represented by formula (2) is smaller than 1%.

The method provided in the present invention further comprises: cooling down the butyl acetate solution that contains azoxystrobin after the reaction is completed, so that azoxystrobin crystal with a structure represented by formula (1) can precipitate from butyl acetate.

Preferably, the method provided in the present invention further comprises: removing salts from the reaction solution that contains butyl acetate after the reaction is completed and before cooling. The purpose of removing salts is to remove water-soluble salt impurities from the reaction solution that contains butyl acetate. The salt removing procedure can comprise: adding water in an appropriate amount into the reaction solution that contains butyl acetate and stirring, separating the aqueous phase from the organic phase by stratification in standing state, and then removing the aqueous phase, to obtain a water-insoluble organic phase. To obtain a better salt removing effect, the salt removing procedure can be repeated for two or more times. The salt removing procedure described above is usually referred to as a water-washing desalting process. There is no particular restriction on the conditions for the water-washing desalting process, which is to say, the process can be executed under conventional conditions in the art. Preferably, corresponding to 100 mol reaction mixture, the usage amount of water is 2-100 ml, and the stirring duration is 0-120 min.; the stratification temperature is 50-100° C., and the standing duration can be determined to allow the organic phase and the oily phase to be separated from each other fully; preferably, the standing duration is 10-120 min.

In the method provided in the present invention, there is no particular restriction on the temperature reached by cooling, which as long as allow the azoxystrobin crystal with a structure represented by formula (1) to precipitate from butyl acetate. Preferably, the temperature reached by cooling is −15° C.~10° C. After cooling, separation can be carried out by filtering, to obtain a filter cake that contains the azoxystrobin crystal with a structure represented by formula (1).

In order to fully remove the impurities that are dissolved in the organic phase, preferably the filter cake can be rinsed with cold butyl acetate. The temperature of butyl acetate used to rinse the filter cake can be −20° C.~10° C.

The preparation method for azoxystrobin provided in the present invention may further comprise: pulping and washing the filter cake with an organic solvent, and then filtering and drying after washing. The organic solvent can be any volatile organic solvent that is commonly used in the art. Preferably, the organic solvent is selected from at least one of petroleum ether, normal hexane, cyclohexane, ethyl acetate, methanol, and ethanol. The drying procedure can be executed at 20-110° C. temperature.

In addition, in the method provided in the present invention, the butyl acetate contained in the filter cake obtained after rinsing with butyl acetate can be removed directly by drying, instead of pulping and washing the filter cake. The drying method can be vacuum drying.

Hereunder the present invention will be further detailed in examples. In the following examples, the yield ratio is calculated with the following method:

Yield ratio of the compound represented by formula (1)=(weight of the compound represented by formula (1)×purity of the compound represented by formula (1)/molecular weight of the compound represented by formula (1))/mole number of the compound represented by formula (2) used The purity of the compound represented by formula (1) is measured with an Agilent gas chromatograph model 6890.

Example 1

This example is to describe the preparation method for azoxystrobin provided in the present invention.

Load 0.105 mol 2-cyanophenol, 0.11 mol anhydrous potassium carbonate, and 100 ml butyl acetate into a 500 ml glass line reactor kettle, heat up to 70° C. while stirring, add 0.1 mol (E)-2-[2-(6-chloropyrimidine-4-methoxy)-phenyl]-3-methoxy methyl acrylate (the compound represented by formula (2), from J&K Chemical Limited, at 95% purity) and a catalyst (0.004 mol 2-methyl-1,4-diazabicyclo[2.2.2]-octane (from Qingdao Hanbing Chemical Co., Ltd., at 99% purity)), continue to heat up the reaction mixture to 105° C. and hold at the temperate for 4 h to perform reaction, and monitor the reaction situation with a gas chromatograph, add 50 ml into the reaction system when the gas chromatograph indicates that the normalized area of (E)-2-[2-(6-chloropyrimidine-4-methoxy)-phenyl]-3-methoxy methyl acrylate is smaller than 1%, after stirring for 60min., and then stand for 10 min. at 80° C. for stratification, remove the aqueous phase, and add water to wash the organic phase again, cool down the obtained organic phase to −5° C. to precipitate crystals, then, filter to obtain 51.3 g wet filter cake, rinse the filter cake with butyl acetate, heat up the rinsed filter cake to approx. 50-60° C. with 100 ml methanol to pulping and wash, and then filter and dry; finally, 37 g yellowish white solid is obtained, and the melting point of the solid is 115-116° C.

Test 10 mg solid product by NMR. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 95.0%, and the purity is 99.5%.

Example 2

This example is to describe the preparation method for azoxystrobin provided in the present invention.

Prepare azoxystrobin according to the method described in example 1, the difference is that the volume of butyl acetate added into the reaction system is 60 ml, and the reaction temperature is 80° C. 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.4%, and the purity is 99.2%.

Example 3

This example is to describe the preparation method for azoxystrobin provided in the present invention.

Prepare azoxystrobin according to the method described in example 1, the difference is that the volume of butyl acetate added into the reaction system is 200 ml, and the reaction temperature is 120° C. 36.8 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.8%, and the purity is 99.4%.

Example 4

This example is to describe the preparation method for azoxystrobin provided in the present invention.

Prepare azoxystrobin according to the method described in example 1, the difference is that the volume of butyl acetate added into the reaction system is 10 ml, and the reaction temperature is 70° C. 35.8 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 92.6%, and the purity is 99.0%.

Example 5

This example is to describe the preparation method for azoxystrobin provided in the present invention.

Prepare azoxystrobin according to the method described in example 1, the difference is that the amount of catalyst added into the reaction system is 0.002 mol. 36.6 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.2%, and the purity is 99.3%.

Example 6

This example is to describe the preparation method for azoxystrobin provided in the present invention.

Prepare azoxystrobin according to the method described in example 1, the difference is that the amount of catalyst added into the reaction system is 0.005 mol. 36.6 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.3%, and the purity is 99.2%.

Example 7

This example is to describe the preparation method for azoxystrobin provided in the present invention.

Prepare azoxystrobin according to the method described in example 1, the difference is that the catalyst is 1,5-diazabicyclo[3.2.2]-nonane (from Qingdao Hanbing Chemical Co., Ltd., at 99% purity). 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.3%, and the purity is 99.4%.

Example 8

This example is to describe the preparation method for azoxystrobin provided in the present invention.

Prepare azoxystrobin according to the method described in example 1, the difference is that the catalyst is 2-methyl-1,4-diazabicyclo[2.2.2]-octane hydrochloride (from Qingdao Hanbing Chemical Co., Ltd., at 99% purity). 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.5%, and the purity is 99.4%.

Example 9

This example is to describe the preparation method for azoxystrobin provided in the present invention.

Prepare azoxystrobin according to the method described in example 1, the difference is that the catalyst is 3-quinuclidone hydrochloride (from Qingdao Hanbing Chemical Co., Ltd., at 99% purity). 36.8 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.7%, and the purity is 99.5%.

Example 10

This example is to describe the preparation method for azoxystrobin provided in the present invention.

Prepare azoxystrobin according to the method described in example 1, the difference is that the catalyst is 1,4-diazabicyclo[2.2.2]-octane (from Qingdao Hanbing Chemical Co., Ltd., at 99% purity). 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.6%, and the purity is 99.3%.

Example 11

This example is to describe the preparation method for azoxystrobin provided in the present invention.

Prepare azoxystrobin according to the method described in example 1, the difference is that 2-cyanophenol is replaced with potassium salt of 2-cyanophenolate in the same molar weight. 36.8 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.5%, and the purity is 99.5%.

Example 12

This example is to describe the preparation method for azoxystrobin provided in the present invention.

Prepare azoxystrobin according to the method described in example 1, the difference is that 2-cyanophenol is replaced with sodium salt of 2-cyanophenolate in the same molar weight. 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.3%, and the purity is 99.4%.

Example 13

This example is to describe the preparation method for azoxystrobin provided in the present invention.

Prepare azoxystrobin according to the method described in example 1, the difference is that the catalyst is 1'-azaspiro[1,3]-dioxolane-2,3'-bicyclo[2.2.2]-octane hydrochloride (from Qingdao Hanbing Chemical Co., Ltd., at 99% purity). 36.4 g yellowish white solid is obtained, and the melting point of the solid is 115-116° C.

Test 10 mg solid product by NMR. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 93.8%, and the purity is 99.2%.

Example 14

This example is to describe the preparation method for azoxystrobin provided in the present invention.

Prepare azoxystrobin according to the method described in example 1, the difference is that the catalyst is 2,6-dimethyl-1,4-diazabicyclo[2.2.2]-octane (from Qingdao Hanbing Chemical Co., Ltd., at 99% purity). 36.7 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.7%, and the purity is 99.2%.

Example 15

This example is to describe the preparation method for azoxystrobin provided in the present invention.

Prepare azoxystrobin according to the method described in example 1, the difference is that the catalyst is 2,5-dimethyl-1,4-diazabicyclo[2.2.2]-octane (from Qingdao Hanbing Chemical Co., Ltd., at 99% purity). 36.6 g yellowish white solid is obtained, and the melting point of the solid is 115-116° C.

Test 10 mg solid product by NMR and MS. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 94.5%, and the purity is 99.3%.

Example 16

This example is to describe the preparation method for azoxystrobin provided in the present invention.

Prepare azoxystrobin according to the method described in example 1, the difference is that the amount of catalyst added into the reaction system is 0.04 mol. 36.3 g yellowish white solid is obtained, and the melting point of the solid is 115-116° C.

Test 10 mg solid product by NMR. The data is $^1$H NMR(500NMR, CDCl$_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 93.6%, and the purity is 99.1%.

Example 17

This example is to describe the preparation method for azoxystrobin provided in the present invention.

Prepare azoxystrobin according to the method described in example 1, the difference is that the operating procedures before the reaction mixture is continued to heat up to 105° C. for reaction are as follows: load 0.105 mol 2-cyanophenol, 0.11 mol anhydrous potassium carbonate, 100 ml butyl acetate, and 0.1 mol (E)-242-(6-chloropyrimidine-4-methoxy)-phenyl]-3-methoxy methyl acrylate into a 500 ml glass line reactor kettle, then heat up to 70° C. while stirring, and stir for 0.5 h at the constant temperature, and then add 0.004 mol 2-methyl-1,4-diazabicyclo[2.2.2]-octane which is acts as the catalyst. Finally, 36 g yellowish white solid is obtained, and the melting point of the solid is 115-116° C.

Test 10 mg solid product by NMR. The data is $^1H$ NMR(500NMR, $CDCl_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 92.8%, and the purity is 99.1%.

Example 18

This example is to describe the preparation method for azoxystrobin provided in the present invention.

Prepare azoxystrobin according to the method described in example 17, the difference is that, after the reaction is completed, filter the hot reaction mixture, wash the obtained filter cake with butyl acetate, cool down the filtered solution to −5° C. and filter, rinse the obtained filter cake with 20 ml cold butyl acetate and then heat the filter cake to pulping and wash with 100 ml methanol, dry the obtained product; finally, 36 g yellowish white solid is obtained, and the melting point of the solid is 115-116° C.

Test 10 mg solid product by NMR. The data is $^1H$ NMR(500NMR, $CDCl_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 92.7%, and the purity is 99.2%.

Comparative Example 1

This comparative example is to describe the preparation methods for azoxystrobin for reference.

Prepare azoxystrobin according to the method described in example 1, the difference is that: the solvent used for the etherification reaction is N,N-dimethyl formamide, the solvent is removed by evaporation at 20 mbar vacuum pressure and 90° C. first after the reaction is completed, to obtain crystals, and then 150 ml butyl acetate is added to dissolve the crystals; next, wash the crystals with water and remove salts from the crystals, and filter, to obtain a filter cake, then, rinse the filter cake with butyl acetate, pulping and wash with an organic solvent, and then filter and dry. Finally, 32.5 g yellowish white solid is obtained, and the melting point of the solid is 115-116° C.

Test 10 mg solid product by NMR and MS. The data is $^1H$ NMR(500NMR, $CDCl_3$): δ 3.64(s, 3H), 3.75(s, 3H), 3.62(s, 2H), 6.42(d, 1H), 7.22(q,1H), 7.29-7.43(m, 5H), 7.49(s, 1H), 7.66(m, 1H), 7.10(q, 1H), 8.40(d, 1H), which fully matches the theoretical value of the compound represented by formula (1), indicating that the product is the compound represented by formula (1).

The calculated yield ratio of the product is 85.3%, and the purity is 97.3%.

It can be seen from examples 1-18: with the preparation method for azoxystrobin provided in the present invention, an azoxystrobin product can be obtained, and the yield ratio of the azoxystrobin product is not lower than 92%, and the purity is not lower than 99%.

It can be seen from the comparison between example 1 and comparative example 1: with the preparation method for azoxystrobin provided in the present invention, the reaction product can precipitate directly from the reaction solvent when butyl acetate is not only used as the reaction solvent but also used as the recrystallization solvent; thus, a reaction solvent removing step can be omitted, and the yield ratio and purity of the obtained azoxystrobin product are higher.

In addition, it can be seen from the comparison between examples 1-3 and example 4: the yield ratio and purity of the obtained azoxystrobin will be higher when the usage amount of butyl acetate is 600-2,000 ml corresponding to 1 mol compound with a structure represented by formula (2) and the reaction happens at 80-120° C. reaction temperature.

It can be seen from the comparison among examples 1, 5, 6, and 16: the yield ratio and purity of the obtained azoxystrobin will be higher when the usage amount of the catalyst is 0.02-0.05 mol corresponding to 1 mol compound with a structure represented by formula (2).

The preferred embodiments of the present invention are described above, but the present invention is not limited to the details in those embodiments. Those skilled in the art can make modifications and variations to the technical scheme of the present invention, without departing from the spirit of the present invention. However, all these modifications and variations shall be deemed as falling into the protection scope of the present invention.

In addition, it should be noted that each of the specific technical features described in above embodiments can be combined in any appropriate form, provided that there is no conflict. The possible combinations are not described specifically in the present invention.

Moreover, different embodiments of the present invention can be combined freely as required, as long as the combinations don't deviate from the ideal and spirit of the present invention. However, such combinations shall also be deemed as falling into the protection scope of the present invention.

The invention claimed is:

1. A preparation method for azoxystrobin with a structure represented by formula (1), comprising:

a) allowing a chemical compound with a structure represented by formula (2) to have an etherification reaction with 2-cyanophenol and/or its salt in a butyl acetate medium, under the catalysis of an azabicyclo-tertiary amine compound and/or its salt that serves as a catalyst, to obtain a butyl acetate solution that contains azoxystrobin;

b) cooling down the butyl acetate solution that contains azoxystrobin;

c) precipitating, by way of the cooling down, the azoxystrobin with a structure represented by formula (1) from the butyl acetate solution, (1)

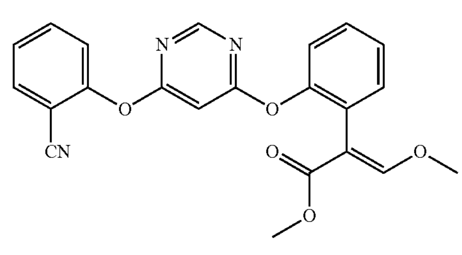

(2)

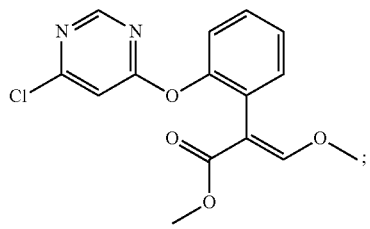

wherein, corresponding to 1 mol compound with a structure represented by formula (2) used in the etherification reaction process, the usage amount of butyl acetate is 600-2,000 ml, and the reaction temperature of the etherification reaction is 80-120° C.

2. The preparation method according to claim 1, wherein, the azabicyclo-tertiary amine compound is at least one of the compound represented by formula (3), the compound represented by formula (4), and the compound represented by formula (5), (3)

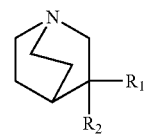

(4)

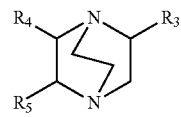

(5)

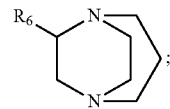

wherein, in formula (3), $R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cyclohydrocarbonyl thioether, cycloalkoxyl, or ketal structure;

in formula (4), $R_3$, $R_4$, and $R_5$ are hydrogen, C1-C6 hydrocarbonyl, C1-C6 oxyl, dimethyl amino, diethyl amino, diisopropyl amino, cyano, fluorine, chlorine, or bromine independently of each other;

in formula (5), $R_6$ is hydrogen, C1-C6 hydrocarbonyl, C1-C6 oxyl, sulfhydryl, dimethyl amino, diethyl amino, diisopropyl amido, cyano, fluorine, chlorine, or bromine independently of each other.

3. The preparation method according to claim 2, wherein, the azabicyclo-tertiary amine compound is at least one of 1-azabicyclo[2.2.2]octane, 1-azabicyclo[2.2.2]octane-8-ketone, 1'-azaspiro[1,3]dioxolane-2,3'-bicyclo[2.2.2]octane, 1,4-diazabicyclo[2.2.2]octane, 2-methyl-1,4-diazabicyclo[2.2.2]octane, 2,6-dimethyl-1,4-diazabicyclo[2.2.2]octane, 2,5-dimethyl-1,4-diazabicyclo[2.2.2]octane, 1,5-diazabicyclo[3.2.2]nonane, and 6-methyl-1,5-diazabicyclo[3.2.2]nonane.

4. The preparation method according to claim 1, wherein, corresponding to 1 mol compound with a structure represented by formula (2) used in the etherification reaction process, the total usage amount of 2-cyanophenol and its salt is 0.9-2 mol.

5. The preparation method according to claim 1, wherein, corresponding to 1 mol compound with a structure represented by formula (2) used in the etherification reaction process, the total usage amount of the azabicyclo-tertiary amine compound and its salt is 0.0005-1 mol.

6. The preparation method according to claim 1, wherein, corresponding to 1 mol compound with a structure represented by formula (2) used in the etherification reaction process, the total usage amount of the azabicyclo-tertiary amine compound and its salt is 0.02-0.05 mol.

* * * * *